(12) United States Patent
Barth et al.

(10) Patent No.: US 7,202,268 B2
(45) Date of Patent: Apr. 10, 2007

(54) DERIVATIVES OF INDOLE-3-CARBOXAMIDE, PREPARATION METHOD THEREOF AND APPLICATION OF SAME IN THERAPEUTICS

(75) Inventors: Francis Barth, Saint-Georges d'Orques (FR); Mireille Rinaldi-Carmona, Saint-Georges d'Orques (FR); Claude Vernhet, Le Triadou (FR)

(73) Assignee: Sanofi-aventis, Paris (FR)

( * ) Notice: Subject to any disclaimer, the term of this patent is extended or adjusted under 35 U.S.C. 154(b) by 0 days.

(21) Appl. No.: 11/138,843

(22) Filed: May 26, 2005

(65) Prior Publication Data

US 2005/0288356 A1    Dec. 29, 2005

Related U.S. Application Data

(63) Continuation of application No. PCT/FR2003/003499, filed on Nov. 27, 2003.

(30) Foreign Application Priority Data

Nov. 29, 2002    (FR) .................................. 02 15086

(51) Int. Cl.
*A61K 31/40* (2006.01)
*A61K 31/405* (2006.01)
*C07D 209/42* (2006.01)
*C07D 209/12* (2006.01)
*C07D 209/18* (2006.01)

(52) U.S. Cl. ........................ 514/415; 514/419; 548/492; 548/493; 548/494; 548/503

(58) Field of Classification Search ................ 548/492, 548/493, 494, 503; 514/415, 419
See application file for complete search history.

(56) References Cited

U.S. PATENT DOCUMENTS 4,973,587 A * 11/1990 Ward et al. .............. 514/235.2

FOREIGN PATENT DOCUMENTS

| WO | WO 01/58869 | 8/2001 |
|---|---|---|
| WO | WO 02/42269 | 5/2002 |

* cited by examiner

*Primary Examiner*—Joseph K. McKane
*Assistant Examiner*—Susannah L. Chung
(74) *Attorney, Agent, or Firm*—Balaram Gupta

(57) ABSTRACT

The invention relates to derivatives of indole-3-carboxamide having general formula (I):

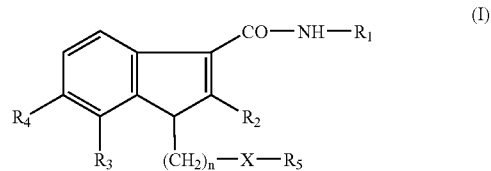

wherein: $R_1$ represents a $C_3$–$C_{10}$ alkyl, a $C_5$–$C_{10}$ carbocyclic radical that is unsubstituted or substituted one or more times with a methyl group; $R_2$ represents a hydrogen atom or a $(C_1$–$C_4)$alkyl group; $R_3$ represents a halogen atom or a $(C_1$–$C_4)$alkyl group; $R_4$ represents a hydrogen or halogen atom or a $(C_1$–$C_4)$alkyl group; $R_5$ represents a $(C_1$–$C_4)$alkyl group or a trifluoromethyl; X represents a sulfur atom, an —$NHSO_2$— group or an —$SO_2$— group; and n is equal to 2 or 3. The invention also relates to a method of preparing the aforementioned derivatives and to the application of same in therapeutics.

11 Claims, No Drawings

DERIVATIVES OF INDOLE-3-CARBOXAMIDE, PREPARATION METHOD THEREOF AND APPLICATION OF SAME IN THERAPEUTICS

This application is a continuation of International application No. PCT/FR2003/003,499, filed Nov. 27, 2003; which claims the benefit of priority of French Patent Application No. 02/15,086, filed Nov. 29, 2002, all of which are incorporated herein by reference in their entirety.

BACKGROUND OF THE INVENTION

1. Field of the Invention

The present invention relates to indole-3-carboxamide derivatives, to the method for preparing them and to the application thereof in therapeutics.

2. Description of the Art

3-Aroylindole derivatives of formula 1:

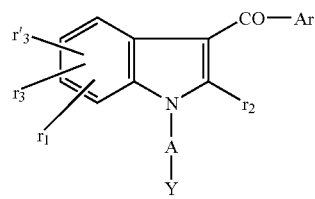

in which $r_1$, $r_2$, $r_3$, $r'_3$, A and Y have various values, are described in international patent application WO 02/42269; these compounds are cannabinoid $CB_2$ receptor agonists.

Indole-3-carboxamide derivatives of formula 2:

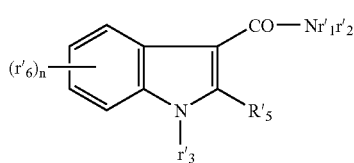

in which $r'_1$, $r'_2$, $r'_3$, $r'_5$, $r'_6$ and n have various values, are described in international patent application WO 01/58869. More particularly, the cannabinoid $CB_2$ receptor-modulating properties of 7-methoxy-1-(2-morpholin-4-ylethyl)-1H-indole-3-carboxamide derivatives are described in Biorg. Med. Chem. Lett., 2002, 12, 2399–2402.

All of the references described hereinabove are incorporated herein by reference in their entirety.

SUMMARY OF THE INVENTION

A subject of the present invention is compounds corresponding to formula (I):

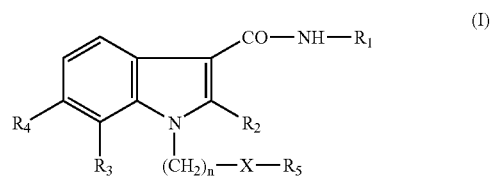

in which
$R_1$ represents:
  a $C_3$–$C_{10}$ alkyl;
  a $C_5$–$C_{10}$ carbocyclic radical that is unsubstituted or substituted one or more times with a methyl group;
$R_2$ represents a hydrogen atom or a $(C_1$–$C_4)$alkyl group;
$R_3$ represents a halogen atom or a $(C_1$–$C_4)$alkyl group;
$R_4$ represents a hydrogen or halogen atom or a $(C_1$–$C_4)$ alkyl group;
$R_5$ represents a $(C_1$–$C_4)$alkyl or trifluoromethyl group;
X represents a sulfur atom, an —$NHSO_2$— group or an —$SO_2$— group;
n is equal to 2 or 3.

The compounds of formula (I) may also exist in the form of hydrates or of solvates, i.e. in the form of associations or of combinations with one or more water molecules or with a solvent. Such hydrates and solvates are also part of the invention.

The compounds of formula (I) may contain one or more asymmetric carbon atoms. The various stereoisomers and also the racemates are part of the invention.

DETAILED DESCRIPTION OF THE INVENTION

In the context of the present invention:
the term "halogen atom" is intended to mean: a fluorine, a chlorine, a bromine or an iodine;
the term "alkyl group" is intended to mean: a linear or branched, saturated aliphatic group. By way of example, mention may be made of methyl, ethyl, propyl, isopropyl, butyl, isobutyl, tert-butyl, n-pentyl, isopentyl, n-hexyl, 1,1-dimethylpropyl or 2,2-dimethylpropyl groups;
the term "$C_5$–$C_{10}$ carbocyclic group" is intended to mean: a monocyclic radical or di- or tricyclic radical that is fused or bridged; the term "monocyclic radical" is intended to mean a cycloalkyl such as, for example, cyclopentyl or cyclohexyl; the expression "di- or tricyclic radical that is fused or bridged" is intended to mean, for example, bicyclo[2.2.1]heptyl, bicyclo[3.2.1]octyl, or adamantyl.

Among the compounds of formula (I), the compounds of the formula (Ia) in which X represents —$NHSO_2$—, the compounds of formula (Ib) in which X represents —$SO_2$—, and the compounds of formula (Ic) in which X represents a sulfur atom are distinguished.

Among the compounds of the invention, preference is given to compounds of formula (I) in which:
$R_1$ represents a $C_5$–$C_8$ carbocyclic radical that is unsubstituted or substituted one or more times with a methyl group;

R₂ represents hydrogen or a (C₁–C₄)alkyl;
R₃ represents a halogen atom or a (C₁–C₄)alkyl group;
R₄ represents a hydrogen or halogen atom or a (C₁–C₄) alkyl group;
R₅ represents a (C₁–C₄)alkyl;
X represents a sulfur atom, an —NHSO₂— group or an —SO₂— group;
n is equal to 2 or 3.

Among the compounds that are the subject of the invention, mention may be made of the preferred compounds, which are defined as follows:
R₁ represents a 1,3,3-trimethylbicyclo[2.2.1]hept-2-yl or a bicyclo[3.2.1]oct-3-yl;
R₂ represents hydrogen or a methyl;
R₃ represents a chlorine, fluorine or bromine atom or a methyl group;
R₄ represents a hydrogen, chlorine or fluorine atom or a methyl group;
R₅ represents a methyl;
n is equal to 3.

Among the compounds that are subjects of the invention, mention may in particular be made of the following compounds:
7-chloro-2-methyl-1-{3-[(methylsulfonyl)amino]-propyl}-N-(1,3,3-trimethylbicyclo[2.2.1]hept-2-yl)-1H-indole-3-carboxamide,
6,7-dichloro-2-methyl-1-{3-[(methylsulfonyl)-amino]propyl}-N-(1,3,3-trimethylbicyclo[2.2.1]hept-2-yl)-1H-indole-3-carboxamide,
7-bromo-2-methyl-1-{3-[(methylsulfonyl)amino]-propyl}-N-(1,3,3-trimethylbicyclo[2.2.1]hept-2-yl)-1H-indole-3-carboxamide,
7-fluoro-2-methyl-1-{3-[(methylsulfonyl)amino]-propyl}-N-(1,3,3-trimethylbicyclo[2.2.1]hept-2-yl)-1H-indole-3-carboxamide,
6,7-difluoro-2-methyl-1-{3-[(methylsulfonyl)-amino]propyl}-N-(1,3,3-trimethylbicyclo[2.2.1]hept-2-yl)-1H-indole-3-carboxamide,
7-chloro-2,6-dimethyl-1-{3-[(methylsulfonyl)-amino]propyl}-N-(1,3,3-trimethylbicyclo[2.2.1]hept-2-yl)-1H-indole-3-carboxamide,
7-bromo-2,6-dimethyl-1-{3-[(methylsulfonyl)amino]-propyl}-N-(1,3,3-trimethylbicyclo[2.2.1]hept-2-yl)-1H-indole-3-carboxamide,
7-fluoro-2,6-dimethyl-1-{3-[(methylsulfonyl)-amino]propyl}-N-(1,3,3-trimethylbicyclo[2.2.1]hept-2-yl)-1H-indole-3-carboxamide,
7-chloro-2-methyl-1-{3-[(methylsulfonyl)amino]-ethyl}-N-(1,3,3-trimethylbicyclo[2.2.1]hept-2-yl)-1H-indole-3-carboxamide,
6,7-dichloro-2-methyl-1-{3-[(methylsulfonyl)-amino]ethyl}-N-(1,3,3-trimethylbicyclo[2.2.1]hept-2-yl)-1H-indole-3-carboxamide,
7-bromo-2-methyl-1-{3-[(methylsulfonyl)amino]-ethyl}-N-(1,3,3-trimethylbicyclo[2.2.1]hept-2-yl)-1H-indole-3-carboxamide,
7-fluoro-2-methyl-1-{3-[(methylsulfonyl)amino]-ethyl}-N-(1,3,3-trimethylbicyclo[2.2.1]hept-2-yl)-1H-indole-3-carboxamide,
6,7-difluoro-2-methyl-1-{3-[(methylsulfonyl)-amino]ethyl}-N-(1,3,3-trimethylbicyclo[2.2.1]hept-2-yl)-1H-indole-3-carboxamide,
7-chloro-2,6-dimethyl-1-{3-[(methylsulfonyl)-amino]ethyl}-N-(1,3,3-trimethylbicyclo[2.2.1]hept-2-yl)-1H-indole-3-carboxamide,
7-bromo-2,6-dimethyl-1-{3-[(methylsulfonyl)amino]-ethyl}-N-(1,3,3-trimethylbicyclo[2.2.1]hept-2-yl)-1H-indole-3-carboxamide,
7-fluoro-2,6-dimethyl-1-{3-[(methylsulfonyl)-amino] ethyl}-N-(1,3,3-trimethylbicyclo[2.2.1]hept-2-yl)-1H-indole-3-carboxamide,
7-chloro-2-methyl-1-{3-(methylsulfonyl)propyl}-N-(1,3,3-trimethylbicyclo[2.2.1]hept-2-yl)-1H-indole-3-carboxamide,
6,7-dichloro-2-methyl-1-{3-(methylsulfonyl)-propyl}-N-(1,3,3-trimethylbicyclo[2.2.1]hept-2-yl)-1H-indole-3-carboxamide,
7-bromo-2-methyl-1-{3-(methylsulfonyl)propyl}-N-(1,3,3-trimethylbicyclo[2.2.1]hept-2-yl)-1H-indole-3-carboxamide,
7-fluoro-2-methyl-1-{3-(methylsulfonyl)propyl}-N-(1,3,3-trimethylbicyclo[2.2.1]hept-2-yl)-1H-indole-3-carboxamide,
6,7-difluoro-2-methyl-1-{3-(methylsulfonyl)-propyl}-N-(1,3,3-trimethylbicyclo[2.2.1]hept-2-yl)-1H-indole-3-carboxamide,
7-chloro-2,6-dimethyl-1-{3-(methylsulfonyl)-propyl}-N-(1,3,3-trimethylbicyclo[2.2.1]hept-2-yl)-1H-indole-3-carboxamide,
7-bromo-2,6-dimethyl-1-{3-(methylsulfonyl)propyl}-N-(1,3,3-trimethylbicyclo[2.2.1]hept-2-yl)-1H-indole-3-carboxamide,
7-fluoro-2,6-dimethyl-1-{3-(methylsulfonyl)-propyl}-N-(1,3,3-trimethylbicyclo[2.2.1]hept-2-yl)-1H-indole-3-carboxamide,
7-chloro-2-methyl-1-{3-(methylsulfonyl)ethyl}-N-(1,3,3-trimethylbicyclo[2.2.1]hept-2-yl)-1H-indole-3-carboxamide,
6,7-dichloro-2-methyl-1-{3-(methylsulfonyl)ethyl}-N-(1,3,3-trimethylbicyclo[2.2.1]hept-2-yl)-1H-indole-3-carboxamide,
7-bromo-2-methyl-1-{3-(methylsulfonyl)ethyl}-N-(1,3,3-trimethylbicyclo[2.2.1]hept-2-yl)-1H-indole-3-carboxamide,
7-fluoro-2-methyl-1-{3-(methylsulfonyl)ethyl}-N-(1,3,3-trimethylbicyclo[2.2.1]hept-2-yl)-1H-indole-3-carboxamide,
6,7-difluoro-2-methyl-1-{3-(methylsulfonyl)ethyl}-N-(1,3,3-trimethylbicyclo[2.2.1]hept-2-yl)-1H-indole-3-carboxamide,
7-chloro-2,6-dimethyl-1-{3-(methylsulfonyl)ethyl}-N-(1,3,3-trimethylbicyclo[2.2.1]hept-2-yl)-1H-indole-3-carboxamide,
7-bromo-2,6-dimethyl-1-{3-(methylsulfonyl)ethyl}-N-(1,3,3-trimethylbicyclo[2.2.1]hept-2-yl)-1H-indole-3-carboxamide,
7-fluoro-2,6-dimethyl-1-{3-(methylsulfonyl)ethyl}-N-(1,3,3-trimethylbicyclo[2.2.1]hept-2-yl)-1H-indole-3-carboxamide,
N-bicyclo[3.2.1]oct-3-yl-7-chloro-2-methyl-1-{3-[(methylsulfonyl)amino]propyl}-1H-indole-3-carboxamide,
N-bicyclo[3.2.1]oct-3-yl-6,7-dichloro-2-methyl-1-{3-[(methylsulfonyl)amino]propyl}-1H-indole-3-carboxamide,
N-bicyclo[3.2.1]oct-3-yl-7-bromo-2-methyl-1-{3[(methylsulfonyl)amino]propyl}-1H-indole-3-carboxamide,
N-bicyclo[3.2.1]oct-3-yl-7-fluoro-2-methyl-1-{3-[(methylsulfonyl)amino]propyl}-1H-indole-3-carboxamide,
N-bicyclo[3.2.1]oct-3-yl-6,7-difluoro-2-methyl-1-{3-[(methylsulfonyl)amino]propyl}-1H-indole-3-carboxamide,
N-bicyclo[3.2.1]oct-3-yl-7-chloro-2,6-dimethyl-1-{3-[(methylsulfonyl)amino]propyl}-1H-indole-3-carboxamide, N-bicyclo[3.2.1]oct-3-yl-7-bromo-2,6-dimethyl-1-{3-[(methylsulfonyl)amino]propyl}-1H-indole-3-carboxamide,
N-bicyclo[3.2.1]oct-3-yl-7-fluoro-2,6-dimethyl-1-{3-[(methylsulfonyl)amino]propyl}-1H-indole-3-carboxamide,
N-bicyclo[3.2.1]oct-3-yl-7-chloro-2-methyl-1-{3-[(methylsulfonyl)amino]ethyl}-1H-indole-3-carboxamide,
N-bicyclo[3.2.1]oct-3-yl-6,7-dichloro-2-methyl-1-{3-[(methylsulfonyl)amino]ethyl}-1H-indole-3-carboxamide,
N-bicyclo[3.2.1]oct-3-yl-7-bromo-2-methyl-1-{3-[(methylsulfonyl)amino]ethyl}-1H-indole-3-carboxamide,
N-bicyclo[3.2.1]oct-3-yl-7-fluoro-2-methyl-1-{3-[(methylsulfonyl)amino]ethyl}-1H-indole-3-carboxamide,
N-bicyclo[3.2.1]oct-3-yl-6,7-difluoro-2-methyl-1-{3-[(methylsulfonyl)amino]ethyl}-1H-indole-3-carboxamide,
N-bicyclo[3.2.1]oct-3-yl-7-chloro-2,6-dimethyl-1-{3-[(methylsulfonyl)amino]ethyl}-1H-indole-3-carboxamide,
N-bicyclo[3.2.1]oct-3-yl-7-bromo-2,6-dimethyl-1-{3-[(methylsulfonyl)amino]ethyl}-1H-indole-3-carboxamide,
N-bicyclo[3.2.1]oct-3-yl-7-fluoro-2,6-dimethyl-1-{3-[(methylsulfonyl)amino]ethyl}-1H-indole-3-carboxamide,
N-bicyclo[3.2.1]oct-3-yl-7-chloro-2-methyl-1-{3-(methylsulfonyl)propyl}-1H-indole-3-carboxamide,
N-bicyclo[3.2.1]oct-3-yl-6,7-dichloro-2-methyl-1-{3-(methylsulfonyl)propyl}-1H-indole-3-carboxamide,
N-bicyclo[3.2.1]oct-3-yl-7-bromo-2-methyl-1-{3-(methylsulfonyl)propyl}-1H-indole-3-carboxamide,
N-bicyclo[3.2.1]oct-3-yl-7-fluoro-2-methyl-1-{3-(methylsulfonyl)propyl}-1H-indole-3-carboxamide,
N-bicyclo[3.2.1]oct-3-yl-6,7-difluoro-2-methyl-1-{3-(methylsulfonyl)propyl}-1H-indole-3-carboxamide,
N-bicyclo[3.2.1]oct-3-yl-7-chloro-2,6-dimethyl-1-{3-(methylsulfonyl)propyl}-1H-indole-3-carboxamide,
N-bicyclo[3.2.1]oct-3-yl-7-bromo-2,6-dimethyl-1-{3-(methylsulfonyl)propyl}-1H-indole-3-carboxamide,
N-bicyclo[3.2.1]oct-3-yl-7-fluoro-2,6-dimethyl-1-{3-(methylsulfonyl)propyl}-1H-indole-3-carboxamide,
N-bicyclo[3.2.1]oct-3-yl-7-chloro-2-methyl-1-{3-(methylsulfonyl)ethyl}-1H-indole-3-carboxamide,
N-bicyclo[3.2.1]oct-3-yl-6,7-dichloro-2-methyl-1-{3-(methylsulfonyl)ethyl}-1H-indole-3-carboxamide,
N-bicyclo[3.2.1]oct-3-yl-7-bromo-2-methyl-1-{3-(methylsulfonyl)ethyl}-1H-indole-3-carboxamide,
N-bicyclo[3.2.1]oct-3-yl-7-fluoro-2-methyl-1-{3-(methylsulfonyl)ethyl}-1H-indole-3-carboxamide,
N-bicyclo[3.2.1]oct-3-yl-6,7-difluoro-2-methyl-1-{3-(methylsulfonyl)ethyl}-1H-indole-3-carboxamide,
N-bicyclo[3.2.1]oct-3-yl-7-chloro-2,6-dimethyl-1-{3-(methylsulfonyl)ethyl}-1H-indole-3-carboxamide,
N-bicyclo[3.2.1]oct-3-yl-7-bromo-2,6-dimethyl-1-{3-(methylsulfonyl)ethyl}-1H-indole-3-carboxamide,
N-bicyclo[3.2.1]oct-3-yl-7-fluoro-2,6-dimethyl-1-{3-(methylsulfonyl)ethyl}-1H-indole-3-carboxamide,
N-1-adamantyl-7-chloro-2-methyl-1-(3-((methyl-sulfonyl)amino)propyl)-1H-indole-3-carboxamide,
7-chloro-2-methyl-1-(3-((methylsulfonyl)amino)-propyl)-N-pentyl-1H-indole-3-carboxamide,
7-chloro-2-methyl-1-(3-(methylthio)propyl)-N-(1,3,3-trimethylbicyclo[2.2.1]hept-2-yl)-1H-indole-3-carboxamide,
7-chloro-1-(3-((methylsulfonyl)amino)propyl)-N-(1,3,3-trimethylbicyclo[2.2.1]hept-2-yl)-1H-indole-3-carboxamide,
6,7-dichloro-1-(3-(methylthio)propyl)-N-(1,3,3-trimethylbicyclo[2.2.1]hept-2-yl)-1H-indole-3-carboxamide,
6,7-dichloro-1-(3-(methylsulfonyl)propyl)-N-(1,3,3-trimethylbicyclo[2.2.1]hept-2-yl)-1H-indole-3-carboxamide,
6,7-dichloro-N-(1,1-dimethylpropyl)-1-(3-(methyl-thio)propyl)-1H-indole-3-carboxamide,
6,7-dichloro-N-(1,1-dimethylpropyl)-1-(3-(methyl-sulfonyl)propyl)-1H-indole-3-carboxamide,
6,7-dichloro-N-(2,2-dimethylpropyl)-1-(3-(methyl-thio)propyl)-1H-indole-3-carboxamide,
6,7-dichloro-N-(2,2-dimethylpropyl)-1-(3-(methyl-sulfonyl)propyl)-1H-indole-3-carboxamide.

More particularly, the following compounds are preferred:
7-chloro-2-methyl-1-{3-[(methylsulfonyl)amino]-propyl}-N-(1,3,3-trimethylbicyclo[2.2.1]hept-2-yl)-1H-indole-3-carboxamide,
6,7-dichloro-2-methyl-1-{3-[(methylsulfonyl)-amino]propyl}-N-(1,3,3-trimethylbicyclo[2.2.1]hept-2-yl)-1H-indole-3-carboxamide, and
7-chloro-2-methyl-1-(3-(methylthio)propyl)-N-(1,3,3-trimethylbicyclo[2.2.1]hept-2-yl)-1H-indole-3-carboxamide.

In accordance with the invention, the compounds of general formula (I) can be prepared according to the process that follows.

This process is characterized in that a functional derivative of indole-3-carboxylic acid of formula (II):

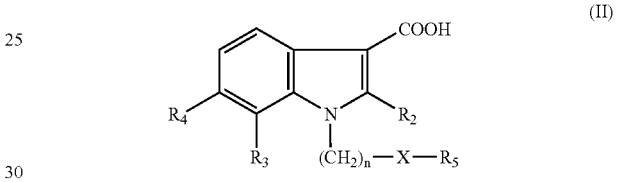

in which $R_2$, $R_3$, $R_4$, $R_5$, X and n are as defined for (I), is treated with an amine of formula $R_1NH_2$ (III).

The expression "functional derivative of an acid of formula (II)" is intended to mean an acid chloride, an anhydride or alternatively the acid opportunistically activated, for example, with benzotriazol-1-yloxytris(dimethylamino)phosphonium hexafluorophosphate (BOP) or (1-benzotriazolyl)oxytris(pyrrolidino)phosphonium hexafluorophosphate (PyBOP).

The reaction is carried out in an aprotic solvent such as dichloromethane, THF or DMF, in a basic medium, and in the presence of a coupling agent such as BOP or dicyclohexylcarbodiimide (DCC).

A compound of formula (I) in which X represents an $SO_2$ group can be prepared from a compound of formula (I) bearing the same substituents and in which X is a sulfur atom, by reacting it with an oxidizing agent such as meta-chloroperbenzoic acid (MCPBA).

The derivatives of indole-3-carboxylic acid of formula (II) are prepared from corresponding indole derivatives of formula (IV):

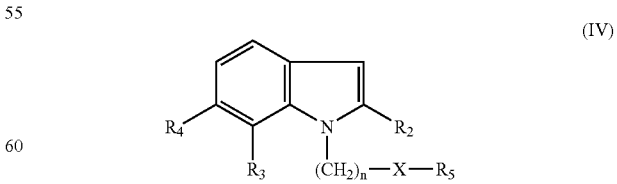

in which $R_2$, $R_3$, $R_4$, $R_5$, X and n are as defined for (I), by reacting it with an acylating agent. The acylating agent may, for example, be oxalyl chloride, or alternatively trichloroacetyl chloride. In the latter case, the intermediate trichloroacetyl derivative obtained is then treated successively with a strong base and then an acid so as to give the desired acid.

The indole derivatives of formula (IV) are known or are prepared by means of processes such as those described in WO 02/42269.

The compounds of formula (II) are novel and constitute a subsequent aspect of the present invention.

Thus, a subject of the present invention is also the compounds of formula (II):

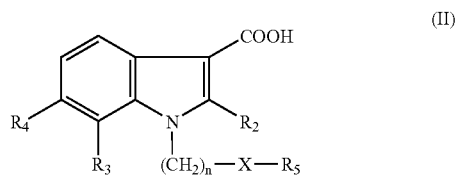

in which:
- $R_2$ represents a hydrogen atom or a $(C_1-C_4)$alkyl group;
- $R_3$ represents a halogen atom or a $(C_1-C_4)$alkyl group;
- $R_4$ represents a hydrogen or halogen atom or a $(C_1-C_4)$ alkyl group;
- $R_5$ represents a $(C_1-C_4)$alkyl or trifluoromethyl group;
- X represents a sulfur atom, an —$NHSO_2$— group or an —$SO_2$— group;
- n is equal to 2 or 3.

The salts and $C_1-C_6$ alkyl esters or the benzyl ester of the compounds of formula (II) are also part of the invention.

Preference is given to the compounds of formula (II) in which:
- $R_2$ represents a hydrogen atom or a methyl group;
- $R_3$ represents a chlorine or bromine atom;
- $R_4$ represents a hydrogen or chlorine atom or a methyl group;
- $R_5$ represents a methyl group;
- X represents a sulfur atom, or an —$NHSO_2$— group;
- n is equal to 3;

and also their salts and $(C_1-C_6)$alkyl esters or benzyl ester.

The following examples describe the preparation of certain compounds in accordance with the invention. These examples are not limiting and merely illustrate the present invention. The numbers of the compounds exemplified refer to those given in the table hereinafter, which illustrates the chemical structures and the physical properties of some compounds according to the invention.

In the examples, the following abbreviations are used:
AT: ambient temperature
DCM: dichloromethane
THF: tetrahydrofuran
TCE: 1,1,2,2-tetrachloroethane.

The nuclear magnetic resonance spectra are recorded at 200 MHz in DMSO-$d_6$. To interpret the spectra, the following abbreviations are used: s: singlet, d: doublet, t: triplet, m: unresolved peak, mt: multiplet, bs: broad singlet, q: quartet, qt: quintet.

The compounds according to the invention are analyzed by LC/UV/MS coupling (liquid chromatography/UV detection/mass spectrometry). The molecular peak (MH+) and the retention time (t) in minutes are measured.

A Waters® MS C18 Symmetry column, sold by Waters, 2.1×50 mm, 3.5 μm, is used at ambient temperature, flow rate 0.4 mL/minute.

The composition of the eluent is as follows:
solvent A: 0.005% of trifluoroacetic acid (TFA) in water,
solvent B: 0.005% of TFA in acetonitrile.
Gradient: the percentage of solvent B ranges from 0 to 90% in 10 minutes with a plateau at 90% of B for 5 minutes.

1 μl of product to be analyzed, at the concentration of 1 mg/ml, is injected.

The UV detection is carried out at 210 nm and the mass detection is carried out in the chemical ionization mode at atmospheric pressure.

EXAMPLE 1

Compound 1

7-Chloro-2-methyl-1-{3-[(methylsulfonyl)amino]propyl}-N-[(1S)-endo-(1,3,3-trimethylbicyclo[2.2.1]hept-2-yl)]-1H-indole-3-carboxamide A) 7-Chloro-2-methyl-1-(3-((methyl-sulfonyl)amino)propyl)-1H-indole-3-carboxylic acid Under nitrogen, 2 g of 7-chloro-2-methyl-1-[3-(methylsulfonylamino)propyl]indole are dissolved in 16 ml of TCE at AT and 0.645 ml of oxalyl chloride in 7 ml of TCE is added. The mixture is heated at 120° C. for 16 hours and then cooled to AT. The reaction medium is diluted by adding 20 ml of water and is then poured onto 50 ml of a 10% HCl solution. The mixture is separated by settling out and the aqueous phase is then washed with DCM. The organic phases are combined and then washed with a saturated NaCl solution. Drying over $Na_2SO_4$ followed by concentration to dryness are performed and the product is purified by chromatography on silica, elution being carried out with $CH_2Cl_2$-MeOH (95/5; v/v). 1.33 g of the expected compound are obtained.

NMR: 1.8–2.0 ppm: m: 2H, 2.7 ppm: s: 3H, 2.9 ppm: s: 3H, 3.1 ppm: q: 2H, 4.5 ppm: bt: 2H, 7.1–7.3 ppm: m: 3H, 8.1 ppm: d: 1H.

B) (7-Chloro-2-methyl-1-{3-[(methylsulfonyl)-amino]propyl}-N-[(1S)-endo-(1,3,3-trimethylbicyclo-[2.2.1]hept-2-yl)]-1H-indole-3-carboxamide Under nitrogen, 0.63 g of the compound of the preceding step are placed in 35 ml of DCM and 0.35 g of (1S)-endo-1,1,3-trimethylbicyclo[2.2.1]heptan-2-ylamine hydrochloride, 0.765 ml of triethylamine and 0.95 g of (1-benzotriazolyl)oxytris(pyrrolidino)phosphonium hexafluorophosphate (PyBOP) are added successively at AT. The mixture is left at AT for 2 hours 15 minutes with stirring, and TLC is performed in order to verify that there is no more starting product. The reaction medium is poured into water and then extracted successively with a solution of $KHSO_4$/$K_2SO_4$, with water, with a 10% sodium hydroxide solution and then with a saturated NaCl solution. Drying is performed over $Na_2SO_4$ and the solvents are evaporated off, and the product is chromatographed a first time on silica, elution being carried out with an EtOAc/cyclohexane (7/3; v/v) mixture. The product obtained is again chromatographed on silica, elution being carried out with EtOAc/cyclohexane (7/3; v/v). 230 mg of product are obtained, M.p.=134–136° C.

NMR: 0.8–2.1 ppm: m: 18H, 2.6 ppm: s: 3H, 2.9 ppm: s: 3H, 3.1 ppm: q: 2H, 3.7 ppm: d: 1H, 4.5 ppm: bt: 2H, 7.0–7.3 ppm: m: 4H, 7.6 ppm: d: 1H.

EXAMPLE 2

Compound 6

7-Chloro-2-methyl-1-(3-(methylthio)propyl)-N-(1,3,3-trimethylbicyclo[2.2.1]hept-2-yl)-1H-indole-3-carboxamide

A) 7-Chloro-2-methyl-1-(3-((methylthio)-propyl)-1H-indole-3-carboxylic acid Under nitrogen, 1.58 g of 7-chloro-2-methyl-1-(3-(methylthio)propyl)indole are dissolved in 16 ml of TCE at AT. 0.602 ml of oxalyl chloride in 8 ml of TCE is added and the mixture is stirred at 120° C. for 16 hours. The reaction medium is concentrated to dryness and then treated with 125 ml of EtOH and 3.5 g of KOH at 80° C. for 16 hours. The product is concentrated to dryness and taken up with EtOAc/$H_2O$, and the organic phase is washed with 10% HCl and then saturated NaCl. The product is dried over $MgSO_4$ and concentrated. 1 g of the expected compound is obtained.

NMR: 1.9–2.2 ppm: m: 5H, 2.6 ppm: t: 2H, 2.8 ppm: s: 3H, 4.6 ppm: m: 2H, 7.1–7.3 ppm: m: 2H, 8.1 ppm: d: 1H, 12.3 ppm: s: 1H.

B) 7-Chloro-2-methyl-1-(3-(methylthio)-propyl)-N-(1,3,3-trimethylbicyclo[2.2.1]hept-2-yl)-1H-indole-3-carboxamide 0.94 g of the acid obtained in the preceding step is mixed with 1.32 ml of triethylamine, 0.6 g of fenchylamine hydrochloride and 1.64 g of PyBOP in 40 ml of TCE. The reaction medium is brought to 100° C. for 1 hour. It is diluted with DCM and washed with a $KHSO_4/K_2SO_4$ buffer. The organic phases are extracted successively with $H_2O$, a 10% NaOH solution and a saturated NaCl solution, and then dried over $MgSO_4$ and concentrated to dryness. The crude product obtained is chromatographed on silica, elution being carried out with a cyclohexane/ethyl acetate (4/1; v/v) mixture. After a second chromatography, elution being carried out with DCM/MeOH (95/5; v/v), 0.8 g of the expected compound is obtained.

EXAMPLE 3

Compound 7

7-Chloro-2-methyl-1-{3-[(methylsulfonyl)-amino]ethyl}-N-(1,3,3-trimethylbicyclo[2.2.1]hept-2-yl)-1H-indole-3-carboxamide 1.06 g of meta-chloroperbenzoic acid (MCPBA) are placed in 30 ml of DCM, the mixture is cooled to +5° C., and 0.73 g of the compound obtained in the preceding example, in 30 ml of DCM, is added. The medium is allowed to return to AT, and is then stirred for 2 and a half hours. The reaction medium is poured onto a 30% NaOH solution, the aqueous phase is washed twice with DCM, and the combined organic phases are then extracted with 10% NaOH, $H_2O$, and then saturated NaCl. The product is dried over $MgSO_4$ and concentrated to dryness. Two successive rounds of chromatography on silica, elution being carried out with cyclohexane/ethyl acetate (3/2; v/v), make it possible to obtain 80 mg of the expected product, M.p.=122° C.

EXAMPLE 4

Compound 4

6.7-Dichloro-2-methyl-1-{3-[(methylsulfonyl)-amino]propyl}-N-(1,3,3-trimethylbicyclo[2.2.1]hept-2-yl)-1H-indole-3-carboxamide

A) 6,7-Dichloro-2-methyl-1-(3-((methylsulfonyl)amino)propyl)-1H-indole-3-carboxylic acid Under nitrogen, 1.87 g of 6,7-dichloro-2-methyl-1-(3-((methylsulfonyl)amino)propyl)indole are dissolved in 14 ml of DCE. 0.54 ml of oxalyl chloride diluted with 7 ml of DCE is added dropwise and the mixture is left to stir for 2 hours at AT. It is then brought to 120° C. for 16 hours. The reaction mixture is concentrated to dryness and taken up with a solution of 3 g of KOH in 120 ml of EtOH and 2 ml of water. It is refluxed for 16 hours. The product is concentrated to dryness and taken up with an EtOAc/$H_2O$ mixture. The organic phase is extracted 3 times with $H_2O$, and the combined aqueous phases are then diluted with EtOAc and acidified with 35% HCl. The organic phase is washed with $H_2O$ and then saturated NaCl. It is dried over $MgSO_4$ and concentrated to dryness. 0.85 g of the expected compound is obtained, NMR: 1.7–2.0 ppm: qt: 2H, 2.7 ppm: s: 3H; 2.85 ppm: s: 3H, 3.0 ppm: q: 2H, 4.4–4.6 ppm: m: 2H; 7.1 ppm: t: 1H; 7.3 ppm: d: 1H, 7.9 ppm: d: 1H, 12.3 ppm: s: 1H.

B) 6,7-Dichloro-2-methyl-1-{3-[(methyl-sulfonyl)amino]propyl}-N-(1,3,3-trimethyl-bicyclo[2.2.1]hept-2-yl)-1H-indole-3-carboxamide 0.84 g of the acid obtained in the preceding step is mixed with 0.925 ml of triethylamine, 0.42 g of fenchylamine hydrochloride and 1.15 g of PyBOP in 35 ml of DCE. The reaction medium is brought to 100° C. for 1 hour, diluted with DCM, and washed with $KHSO_4/K_2SO_4$ buffer, then $H_2O$, 10% NaOH and, finally, NaCl. The product is dried over $MgSO_4$ and concentrated to dryness. The crude product obtained is chromatographed on silica, elution being carried out with a DCM/MeOH (99/1; v/v) mixture. 0.52 g of the expected compound is obtained, M.p.=150–154° C.

By carrying out the procedure described in Example 1, step A (Preparation 1), in Example 2, step A (Preparation 2) and in Example 4, step A (Preparation 3), the intermediate acids of formula (II) described in the Table 1 below are prepared:

TABLE 1

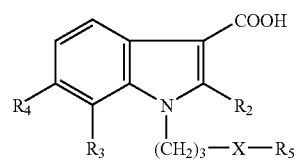

(II)

| Preparations | $R_2$ | $R_3$ | $R_4$ | X—$R_5$ | Characterization |
|---|---|---|---|---|---|
| 4 | Me | Br | Me | $NHSO_2Me$ | NMR: 1.8–2.0 ppm: m: 2H; 2.4 ppm: s: 3H; 2.75 ppm: s: 3H; 2.9 ppm: s: 3H; 3.1 ppm: q: 2H; 4.6 ppm: m: 2H; 7.1 ppm: m: 2H; 7.9 ppm: d: 1H; 12.1 ppm: s: 1H. |

TABLE 1-continued (II) Structure: indole with COOH at 3-position, R2 at 2-position, N-(CH2)3-X-R5, R3 and R4 on benzene ring.

| Preparations | R2 | R3 | R4 | X—R5 | Characterization |
|---|---|---|---|---|---|
| 5 | H | Cl | H | NHSO2Me | NMR: 2.0 ppm: qt: 2H; 2.9 ppm: s: 3H; 2.95 ppm: q: 2H; 4.6 ppm: t: 2H; 7.0–7.2 ppm: m: 2H; 7.3 ppm: d: 1H; 8.05 ppm: d: 1H; 8.15 ppm: s: 1H; 12.2 ppm: s: 1H. |
| 6 | H | Cl | Cl | SMe | NMR: 2–2.2 ppm: m: 5H; 2.4–2.6 ppm: m: 2H; 4.6 ppm: t: 2H; 7.4 ppm: d: 1H; 8.05 ppm: d: 1H; 8.2 ppm: s: 1H; 12.4 ppm: s: 1H. |

The Table 2 that follows illustrates the chemical structures and the properties of some examples of compounds according to the invention. In this Table 2, Me represents a methyl group and t-Bu represents a t-butyl group.

TABLE 2

(I) Structure: indole with CO—NH—R1 at 3-position, R2 at 2-position, N-(CH2)3-X-R5, R3 and R4 on benzene ring.

| Compounds | R1 | R2 | R3 | R4 | —XR5 | Characterization |
|---|---|---|---|---|---|---|
| 1 | bicyclic Me,Me,Me 1(S) endo | Me | Cl | H | NHSO2Me | NMR |
| 2 | bicyclic (bicyclo[2.2.2]) | Me | Cl | H | NHSO2Me | MH+ = 452.2 t = 8.81 |
| 3 | adamantyl | Me | Cl | H | NHSO2Me | M.p. = 178–180° C. |
| 4 | bicyclic Me,Me,Me 1(S) endo | Me | Cl | Cl | NHSO2Me | M.p. = 150–154° C. |
| 5 | bicyclo[2.2.2] | Me | Br | Me | NHSO2Me | M.p. = 191–193° C. |
| 6 | bicyclic Me,Me,Me 1(S) endo | Me | Cl | H | SMe | MH+ = 433.3 t = 11.66 |
| 7 | bicyclic Me,Me,Me 1(S) endo | Me | Cl | H | SO2Me | M.p. = 122° C. |
| 8 | bicyclic Me,Me,Me 1(S) endo | H | Cl | H | NHSO2Me | M.p. = 161–162° C. |
| 9 | bicyclic Me,Me,Me 1(S) endo | H | Cl | Cl | SMe | M.p. = 62° C. |
| 10 | bicyclic Me,Me,Me 1(S) endo | H | Cl | Cl | SO2Me | M.p. = 89–92° C. |
| 11 | n-pentyl | Me | Cl | H | NHSO2Me | MH+ = 414.2 t = 8.11 |
| 12 | —C(CH3)2Et | H | Cl | Cl | SMe | M.p. = 100–103° C. |
| 13 | —CH2—tBu | H | Cl | Cl | SMe | M.p. = 170–173° C. |
| 14 | —C(CH3)2Et | H | Cl | Cl | SO2Me | M.p. = 123 = 126° C. |
| 15 | —CH2—tBu | H | Cl | Cl | SO2Me | M.p. = 208–211° C. |

The compounds according to the invention are the subject of pharmacological assays.

The compounds according to the invention show good affinity, in vitro, for cannabinoid ($CB_2$) receptors and a clearly lower affinity, in vitro, for cannabinoid ($CB_1$) receptors, whether they are human receptors or rodent receptors. The binding affinity assays are carried out according to the experimental conditions described by Devane et al (Molecular Pharmacology, 1988, 34, 605–613) with membranes derived from cell lines in which the $CB_1$ receptors (Matsuda et al., Nature 1990, 346, 561–564) and $CB_2$ receptors (Munro et al., Nature 1993, 365, 61–65) are expressed. For the human receptors, the in vitro affinity for $CB_2$ cannabinoids, expressed in the form of Ki (inhibition constant), is less than $10^{-7}$ M, and the ratio of the affinity for $CB_1$ receptors to that for $CB_2$ receptors is at least 100.

Furthermore, the compounds according to the invention behave, in vitro, like agonists specific for human cannabinoid $CB_2$ receptors versus cannabinoid $CB_1$ receptors; they decrease the production of cAMP in cells stimulated with forskolin, by inhibiting adenylate cyclase. The assays are carried out according to the experimental conditions described by Matsuda et al., Nature 1990, 346, 561–564.

It therefore appears that the compounds according to the invention have a selective agonist activity with respect to cannabinoid $CB_2$ receptors.

The compounds according to the invention, or their possible salts, also have an affinity, in vivo, for cannabinoid $CB_2$ receptors present in mouse spleen when they are administered intravenously or orally. Their activity is demonstrated by means of ex vivo $[^3H]$-CP 55940 binding experiments. The assays are carried out according to the experimental conditions described by M. Rinaldi-Carmona et al., Life Sciences, 1995, 56, 1941–1947.

The compounds according to the invention can therefore be used for preparing medicinal products, in particular medicinal products that are cannabinoid $CB_2$ receptor agonists.

Thus, according to another of its aspects, a subject of the invention is medicinal products which comprise a compound of formula (I) or a hydrate or a solvate of the compound of formula (I).

These medicinal products are of use in therapeutics, in particular in the treatment and prevention of the following conditions:

autoimmune hemolytic anemia, multiple sclerosis, amyotrophic lateral sclerosis, amyloses, glomerulonephritis, transplant rejection, diseases affecting the plasmacytic line; allergic diseases: delayed or immediate hypersensitivity, allergic rhinitis, contact dermatitis, allergic conjunctivitis; parasitic, viral or bacterial infectious diseases: AIDS, meningitis;

inflammatory diseases, in particular diseases of the joints: arthritis, rheumatoid arthritis, reactional arthritis, osteoarthritis, spondylitis, ankylosing spondyloarthritis, undifferentiated spondyloarthritis, gout, vasculitis, thyroiditis, Behcet's disease, Crohn's disease, inflammatory bowel disease (IBD) and irritable bowel syndrome (IBS);

osteoporosis; pain: chronic pain of the inflammatory type, neuropathic pain, acute peripheral pain; ocular conditions; ocular hypertension, glaucoma; pulmonary conditions: respiratory tract diseases, asthma, chronic bronchitis, chronic obstructive pulmonary disease (COPD), emphysema; central nervous system diseases and neurodegenerative diseases: Tourette's syndrome, Parkinson's disease, Alzheimer's disease, senile dementia, chorea, Huntington's chorea, epilepsy, psychoses, depression, spinal cord lesions; migraine, dizziness, vomiting, nausea, in particular nausea subsequent to chemotherapy; cardiovascular disease, in particular hypertension, arteriosclerosis, heart attack, cardiac ischemia; renal ischemia; cancers: benign skin tumors, cancerous tumors and papillomas, lung cancers and small cell lung cancers, prostate tumors, brain tumors (glioblastomas, medulloepitheliomas, medulloblastomas, neuroblastomas, tumors of embryonic origin, astrocytomas, astroblastomas, ependymomas, oligodendrogliomas, plexus tumors, neuroepitheliomas, epiphyseal tumors, ependymoblastomas, neuroectodermal tumors, malignant meningiomas, sarcomatosis, malignant melanomas, schwannomas; gastrointestinal diseases, obesity, immune system disorders, in particular autoimmune diseases: psoriasis, lupus erythematosus, connective tissue diseases or connectivitis, contact dermatitis, Sjögren's syndrome, Guillain-Barré syndrome; cirrhoses and chronic liver cirrhoses.

According to another of its aspects, the present invention relates to pharmaceutical compositions comprising, as active principle, a compound according to the invention. These pharmaceutical compositions contain an effective dose of at least one compound according to the invention or a hydrate or solvate of said compound, and also at least one pharmaceutically acceptable excipient.

Said excipients are chosen, according to the pharmaceutical form and the method of administration desired, from the usual excipients that are known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or an optional solvate or hydrate thereof, can be administered in a unit administration form, as a mixture with conventional pharmaceutical excipients, to animals and to human beings for the prophylaxis or the treatment of the conditions or the diseases above.

Suitable unit administration forms comprise oral forms such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

When given orally, the dose of active principle administered per day can reach 0.01 to 20 mg/kg, taken in one or more doses.

There may be specific cases where higher or lower doses are appropriate; such dosages do not depart from the context of the invention. According to the usual practice, the dosage appropriate for each patient is determined by the physician according to the method of administration and the weight and response of said patient.

According to another of its aspects, the present invention also relates to a method for treating the pathologies indicated above, which comprises the administration, to a patient, of an effective dose of a compound according to the invention or hydrates or solvates.

What is claimed is:
1. A compound of formula (I):

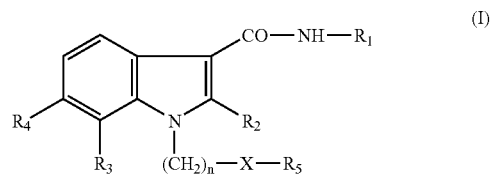

wherein:
$R_1$ is $C_3$–$C_{10}$ alkyl; or
a $C_5$–$C_{10}$ carbocyclic radical that is unsubstituted or substituted one or more times with methyl;

R$_2$ is hydrogen or (C$_1$–C$_4$)alkyl;
R$_3$ is halogen or (C$_1$–C$_4$)alkyl;
R$_4$ is hydrogen, halogen or (C$_1$–C$_4$)alkyl;
R$_5$ is (C$_1$–C$_4$)alkyl or trifluoromethyl;
X is sulfur, —NHSO$_2$— or —SO$_2$—; and
n is equal to 2 or 3;
or a hydrate or a solvate thereof, or an enantiomer, a stereoisomer or a racemate thereof.

2. The compound of formula (I) as set forth in claim 1, wherein:
R$_1$ is 1,3,3-trimethylbicyclo[2.2.1]hept-2-yl or bicyclo [3.2.1]oct-3-yl;
R$_2$ is hydrogen or methyl;
R$_3$ is chlorine, fluorine, bromine or methyl;
R$_4$ is hydrogen, chlorine, fluorine or methyl; and
R$_5$ is methyl;
or a hydrate or a solvate thereof, or an enantiomer, a stereoisomer or a racemate thereof.

3. The compound of formula (I) as set forth in claim 1, which is chosen from:
7-chloro-2-methyl-1-{3-[(methylsulfonyl)amino]-propyl}-N-[(1S)-endo-(1,3,3-trimethylbicyclo-[2.2.1]hept-2-yl)-1H-indole-3-carboxamide;
6,7-dichloro-2-methyl-1-{3-[(methylsulfonyl)-amino]propyl}-N-(1,3,3-trimethylbicyclo[2.2.1]hept-2-yl)-1H-indole-3-carboxamide; and
7-chloro-2-methyl-1-(3-(methylthio)propyl)-N-(1,3,3-trimethylbicyclo[2.2.1]hept-2-yl)-1H-indole-3-carboxamide;
or a hydrate or a solvate thereof, or an enantiomer, a stereoisomer or a racemate thereof.

4. A process for preparing a compound of formula (I):

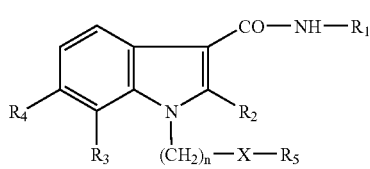

wherein:
R$_1$ is C$_3$–C$_{10}$ alkyl; or
a C$_5$–C$_{10}$ carbocyclic radical that is unsubstituted or substituted one or more times with methyl;
R$_2$ is hydrogen or (C$_1$–C$_4$)alkyl;
R$_3$ is halogen or (C$_1$–C$_4$)alkyl;
R$_4$ is hydrogen, halogen or (C$_1$–C$_4$)alkyl;
R$_5$ is (C$_1$–C$_4$)alkyl or trifluoromethyl;
X is sulfur, —NHSO$_2$— or —SO$_2$—; and
n is equal to 2 or 3;
said process comprising:
reacting a functional derivative of indole-3-carboxylic acid of formula (II):

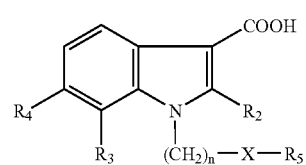

wherein R$_2$, R$_3$, R$_4$, R$_5$, X and n are as defined above, with an amine of formula R$_1$NH$_2$ (III), wherein R$_1$ is as defined above.

5. The process as set forth in claim 4, wherein:
R$_1$ is 1,3,3-trimethylbicyclo[2.2.1]hept-2-yl or bicyclo [3.2.1]oct-3-yl;
R$_2$ is hydrogen or methyl;
R$_3$ is chlorine, fluorine, bromine or methyl;
R$_4$ is hydrogen, chlorine, fluorine or methyl; and
R$_5$ is methyl.

6. The process as set forth in claim 4, wherein the compound of formula (I) is selected from the group consisting of:
7-chloro-2-methyl-1-{3-[(methylsulfonyl)amino]-propyl}-N-[(1S)-endo-(1,3,3-trimethylbicyclo-[2.2.1]hept-2-yl)-1H-indole-3-carboxamide;
6,7-dichloro-2-methyl-1-{3-[(methylsulfonyl)-amino]propyl}-N-(1,3,3-trimethylbicyclo[2.2.1]hept-2-yl)-1H-indole-3-carboxamide; and
7-chloro-2-methyl-1-(3-(methylthio)propyl)-N-(1,3,3-trimethylbicyclo[2.2.1]hept-2-yl)-1H-indole-3-carboxamide.

7. A compound of formula (II):

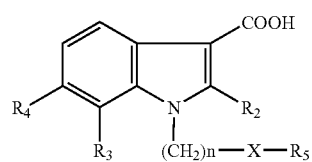

wherein:
R$_2$ is hydrogen or (C$_1$–C$_4$)alkyl;
R$_3$ is halogen or (C$_1$–C$_4$)alkyl;
R$_4$ is hydrogen, halogen or (C$_1$–C$_4$)alkyl;
R$_5$ is (C$_1$–C$_4$)alkyl or trifluoromethyl;
X is sulfur, —NHSO$_2$— or —SO$_2$—; and
n is equal to 2 or 3;
or a salt, C$_1$–C$_6$ alkyl ester or a benzyl ester thereof.

8. The compound of formula (II) as set forth in claim 7 wherein:
R$_2$ is hydrogen or methyl;
R$_3$ is chlorine or bromine;
R$_4$ is hydrogen, chlorine or methyl;
R$_5$ is methyl;
X is sulfur or —NHSO$_2$—; and
n is equal to 3,
or a salt, C$_1$–C$_6$ alkyl ester or a benzyl ester thereof.

9. A pharmaceutical composition comprising one or more compounds of formula (I) as set forth in claim 1, including a hydrate or a solvate thereof, or an enantiomer, a stereoisomer or a racemate thereof, in combination with at least one pharmaceutically acceptable excipient.

10. The composition as set forth in claim 9, wherein:
R$_1$ is 1,3,3-trimethylbicyclo[2.2.1]hept-2-yl or bicyclo [3.2.1]oct-3-yl;
R$_2$ is hydrogen or methyl;
R$_3$ is chlorine, fluorine, bromine or methyl;
R$_4$ is hydrogen, chlorine, fluorine or methyl; and
R$_5$ is methyl.

11. The composition as set forth in claim 9, wherein the compound of formula (I) is selected from the group consisting of:

7-chloro-2-methyl-1-{3-[(methylsulfonyl)amino]-propyl}-N-[(1S)-endo-(1,3,3-trimethylbicyclo-[2.2.1]hept-2-yl)-1H-indole-3-carboxamide;

6,7-dichloro-2-methyl-1-{3-[(methylsulfonyl)-amino]propyl}-N-(1,3,3-trimethylbicyclo[2.2.1]hept-2-yl)-1H-indole-3-carboxamide; and 7-chloro-2-methyl-1-(3-(methylthio)propyl)-N-(1,3,3-trimethylbicyclo[2.2.1]hept-2-yl)-1H-indole-3-carboxamide.

* * * * *